Figure 1:
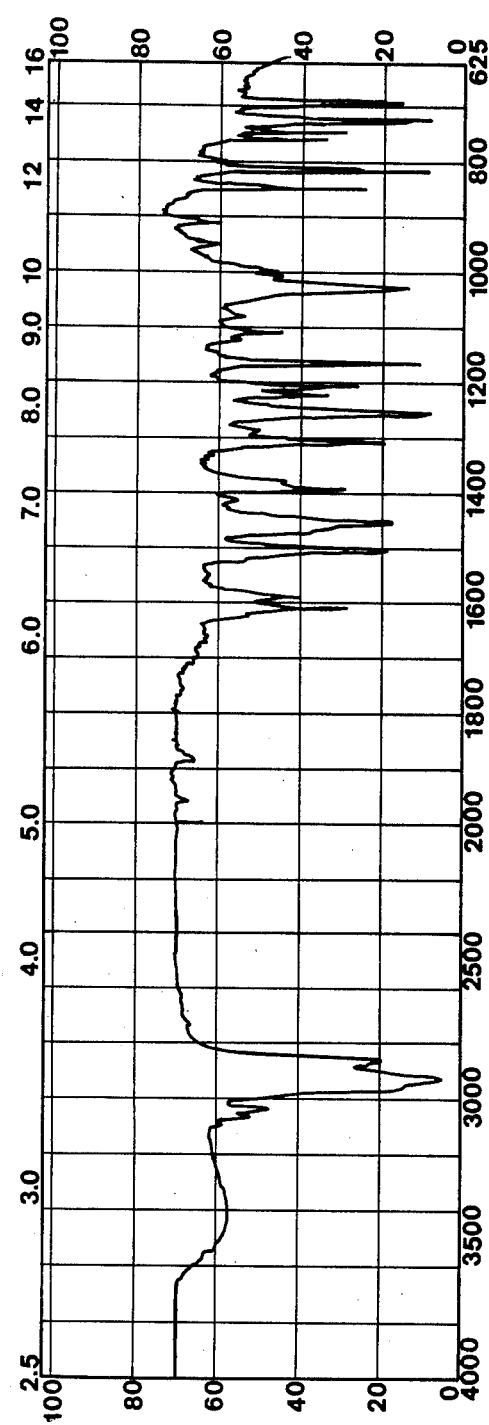

United States Patent [19]

Del Conte

[11] 4,239,920

[45] Dec. 16, 1980

[54] PROCESS FOR PREPARING 6-ISOBORNYL-3,4-XYLENOL

[75] Inventor: Maria L. Del Conte, Trieste, Italy

[73] Assignee: Farmatis, S.p.A., Milan, Italy

[21] Appl. No.: 24,208

[22] Filed: Mar. 27, 1979

[51] Int. Cl.$^3$ .......................... C07C 39/15; C07C 39/17
[52] U.S. Cl. ..................................... 568/734; 568/743
[58] Field of Search ................ 568/731, 721, 734, 743

[56] References Cited

U.S. PATENT DOCUMENTS

| 2,537,647 | 1/1951 | Kitchen | 568/734 |
| 3,833,671 | 9/1974 | Mardiguian et al. | 568/734 |
| 3,878,254 | 4/1975 | Gazave | 568/734 |

FOREIGN PATENT DOCUMENTS

| 2032170 | 1/1971 | Fed. Rep. of Germany | 568/734 |
| 1133959 | 7/1969 | United Kingdom | 568/734 |
| 1206774 | 9/1970 | United Kingdom | 568/734 |

*Primary Examiner*—Werren B. Lone

[57] ABSTRACT

A process for preparing 6-isobornyl-3,4-xylenol by condensing camphene and 3,4-dimethylphenol benzylether in an inert anhydrous organic solvent in the presence of a Friedel-Crafts catalyst at a temperature of around 0° C., and the 6-isobornyl-3,4-xylenol benzylether thus obtained is debenzylated by hydrogenating in the presence of a solvent and a hydrogenation catalyst.

4 Claims, 6 Drawing Figures

PROCESS FOR PREPARING 6-ISOBORNYL-3,4-XYLENOL

This invention relates to a new process for the economical industrial production of high-purity 6-isobornyl-3,4-xylenol (xybornol).

Xybornol is a product of formula

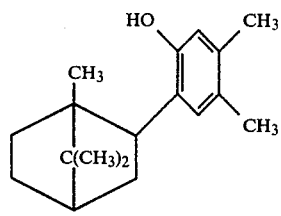

which has been known for some years as a powerful antibacterial substance. Only two methods are known for preparing this product. The first (British Pat. No. 1,206,774/1970) comprises reacting camphene with 3,4-xylenol at a temperature of 70–80° C. in the presence of $SnCl_4$ as catalyst.

In this reaction a mixture is formed of the two isomers 6-isobornyl-3,4-xylenol and 6-hexo-isocamphanyl-3,4-xylenol, and these can be separated only by chromatography with an alumina column, using benzene as eluent. This process cannot be considered an industrial process, both because of the chromatographic separation stage which it comprises, and because it enables the 6-isobornyl-3,4-xylenol to be prepared only with very low yields.

The second known process (DT-OS 2032170/1971) comprises reacting camphene with a strong excess of 3,4-xylenol methylether, in order to constitute a reaction medium and enable the process to be carried out at a temperature less than the melting point of the camphene. The xybornol methylether obtained in this manner is separated, purified and then demethylated with hydrobromic acid in anhydrous acetic acid. The total overall yield is around 50% in terms of useful product.

This very complicated process, which gives rather modest yields, is the best process known at the present time.

We have now discovered, in accordance with the present invention, a new industrial process for extremely simply and economically producing xybornol with a very high yield of practically pure product.

The new process consists essentially of reacting camphene with 3,4-xylenol benzylether in an anhydrous organic solvent in the presence of a Friedel-Crafts catalyst at a temperature of around 0° C. The xybornol benzylether obtained in this manner is debenzylated by hydrogenation in the presence of a preferably acid hydrogenation solvent, with a hydrogenation catalyst. The new process is represented by the following reaction scheme:

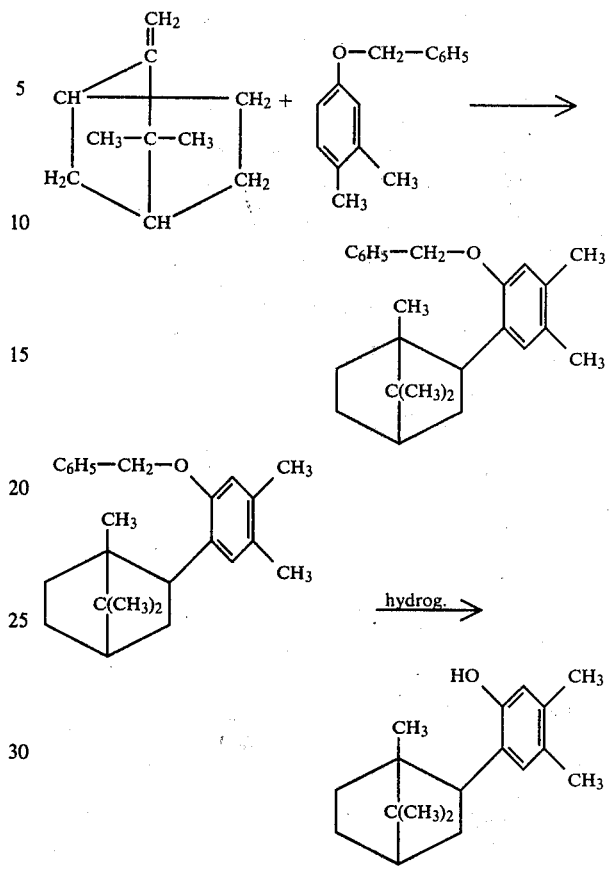

The starting substance used in the present process, namely 3,4-xylenol benzylether, is a new product which also forms part of the present invention. The process according to the present invention is characterised by being extremely selective towards the production of 6-isobornyl-3,4-xylenol, without simultaneous production of the 6-hexo-isocamphanyl-3,4-xylenol isomer, the elimination of which from the mixture would be extremely difficult. In this respect, we have found that if instead of reacting the camphene directly with 3,4-xylenol it is reacted with its benzylether under critical conditions constituted by a catalyst of the Friedel-Crafts type in an inert anhydrous organic solvent and a temperature of around 0° C., at least 90% of the reaction mixture obtained surprisingly consists of xybornol benzylether, the rest being constituted by unreacted starting substances which are easily eliminated by the common chemical purification processes.

The solvent used for the reaction between the camphene and ether can be carbon disulphide, carbon tetrachloride, $CH_2Cl_2$, ethyl ether, benzene, nitrobenzene or in general any solvent suitable for the Friedel-Crafts synthesis. Any Lewis acid generally used as a Friedel-Crafts catalyst can be equally well used as the condensation catalyst.

Suitable catalysts are for example $SnCl_4$, $BF_3$, $AlCl_3$, $SbCl_5$.

The debenzylation of the xybornol benzylether can be carried out under the usual conditions, preferably in ethyl acetate and acetic acid with very small percentages of perchloric acid, using a catalyst consisting of Pd on carbon.

However one can equally well operate in a medium constituted by any hydrogenation solvent, preferably acid in order to increase the reaction velocity, and using a catalyst chosen from the group consisting of Ph, Pt and their compounds.

Under optimum reaction conditions, yields of very pure xybornol close to 100% are obtained.

The reaction solvents can be recovered.

The xybornol benzylether does not require severe purification, and can be hydrogenated in the state in which it is obtained in the first stage of the process.

With respect to the process of the known art which uses as its starting substance 3,4-xylenol methylether and which, as stated, in the best process known at the present time, the new process according to the invention has the advantage (a) of not requiring as its reaction medium an excess of ether which has obviously to be recovered and recycled when the reaction is terminated, and which represents a considerable burden to the processing cycle without on the other hand avoiding large losses of valuable product;

(b) of avoiding the drastic hydrolysis of the ether by HBr and glacial acetic acid, this hydrolysis being to a large extent responsible for the low yields obtained by this process.

The 3,4-xylenol benzylether used as the starting substance in the present process is prepared by reacting 3,4-dimethylphenol, in an inert organic solvent, with a reactive benzyl derivative such as a halide or ester, preferably the bromide.

Preferably the reaction is carried out in an aliphatic alcohol such as methyl or ethyl alcohol, in the presence of an alkaline hydrate.

In order to make the process according to the present invention more easily reproducible, one practical example is described hereinafter as a non-limiting illustration only.

EXAMPLE

Preparation of 3,4-dimethylphenol benzylether.

16.5 grams of NaOH are dissolved in 200 ml of methyl alcohol, and 50 g of 3,4-dimethylphenol are added to this solution.

When completely dissolved, 70 g of benzyl bromide are added slowly, under cooling with ice. The mixture is left overnight at ambient temperature. A precipitate is formed which is filtered, washed with water, and then with a little methanol.

It is dried cold under vacuum.

79 g of 3,4-dimethylphenol benzylether are obtained with a purity of 98% (yield 91%).

After crystallising from methanol, the product has the following characteristics:

M.P.=45° C.

Rf=0.5 (TLC with benzene:hexane 1:1 eluent-unitary product)

I.R.: see FIG. 1.

Figure 2:
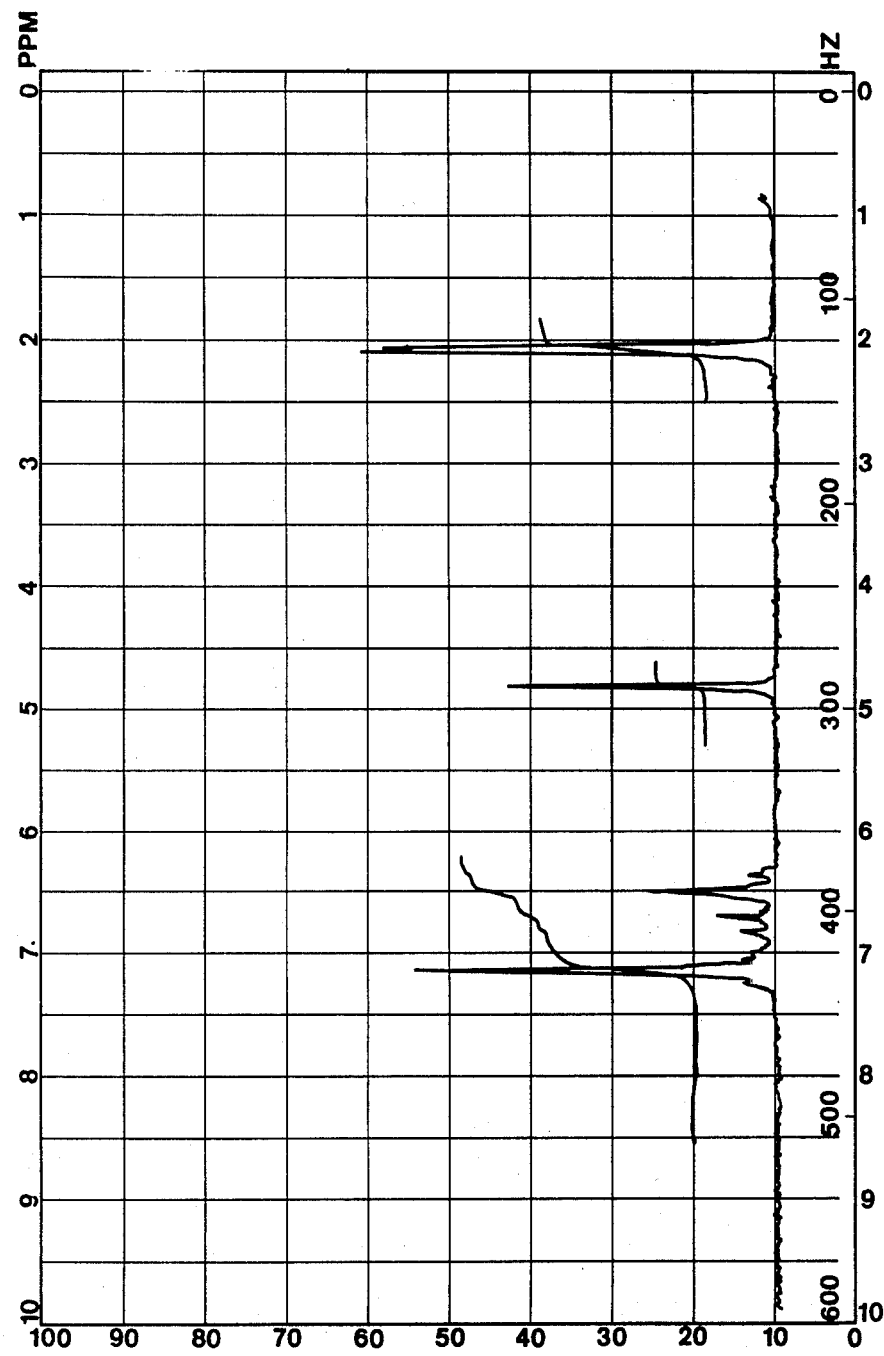

NMR: see FIG. 2—The following signals are observed (d values), CDCl$_3$ solvent: 2.10 and 2.12 (6H, 2 singlets, aromatic methyls) 4.86 (2H, singlet, benzylic CH$_2$) 6.3-7 (3H, complex system, aromatic hydrogens) 7.2 (5H, wide singlet, C$_6$H$_5$)

Preparation of xybornol benzylether 13.6 grams of camphene and 21.2 g of 3,4-dimethylphenol benzylether are dissolved in 20 ml of anhydrous carbon disulphide. The mixture is cooled to 0° C. and 2 ml of SnCl$_4$ are added under agitation.

The solution is then left at 0° C. for 30 h. At the end of this time, it is poured into 100 ml of iced water and extracted twice with petroleum ether. The organic extract is washed with a 5% NaCHO$_3$ solution, and then with water. The solvent is evaporated, and a residue is obtained consisting of 32 g of product having a purity greater than 90% (yield 92%).

After crystallising from methanol, the product has the following characteristics:

M.P.=106° C.

Rf=0.8 (TLC with benzene:hexene 1:1 eluent—unitary product)

Figure 3:
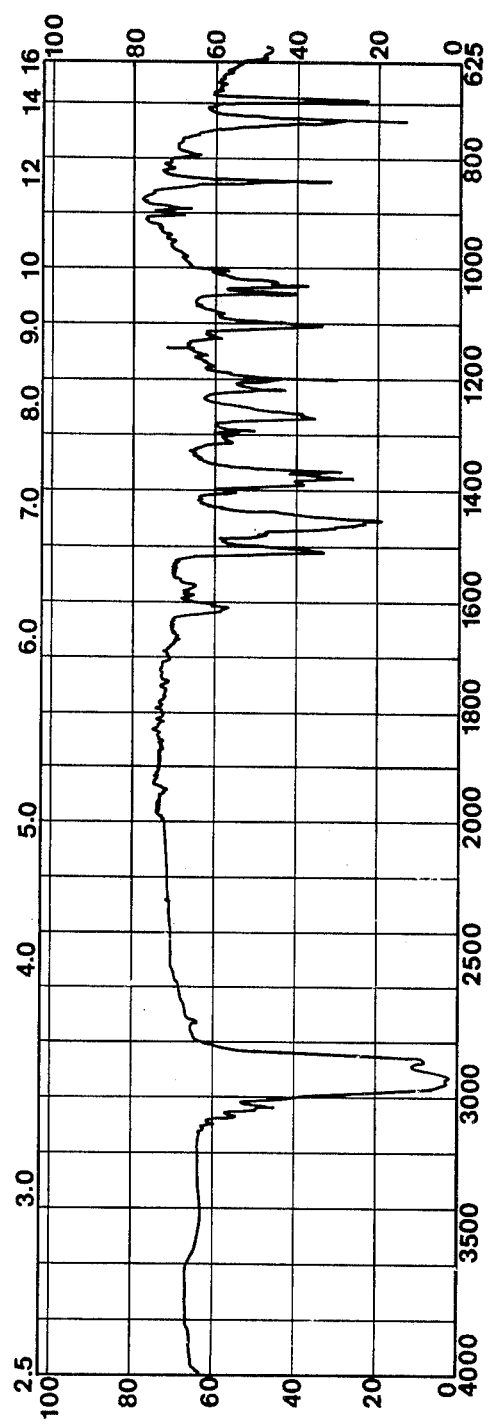

I.R.: See FIG. 3

Figure 4:
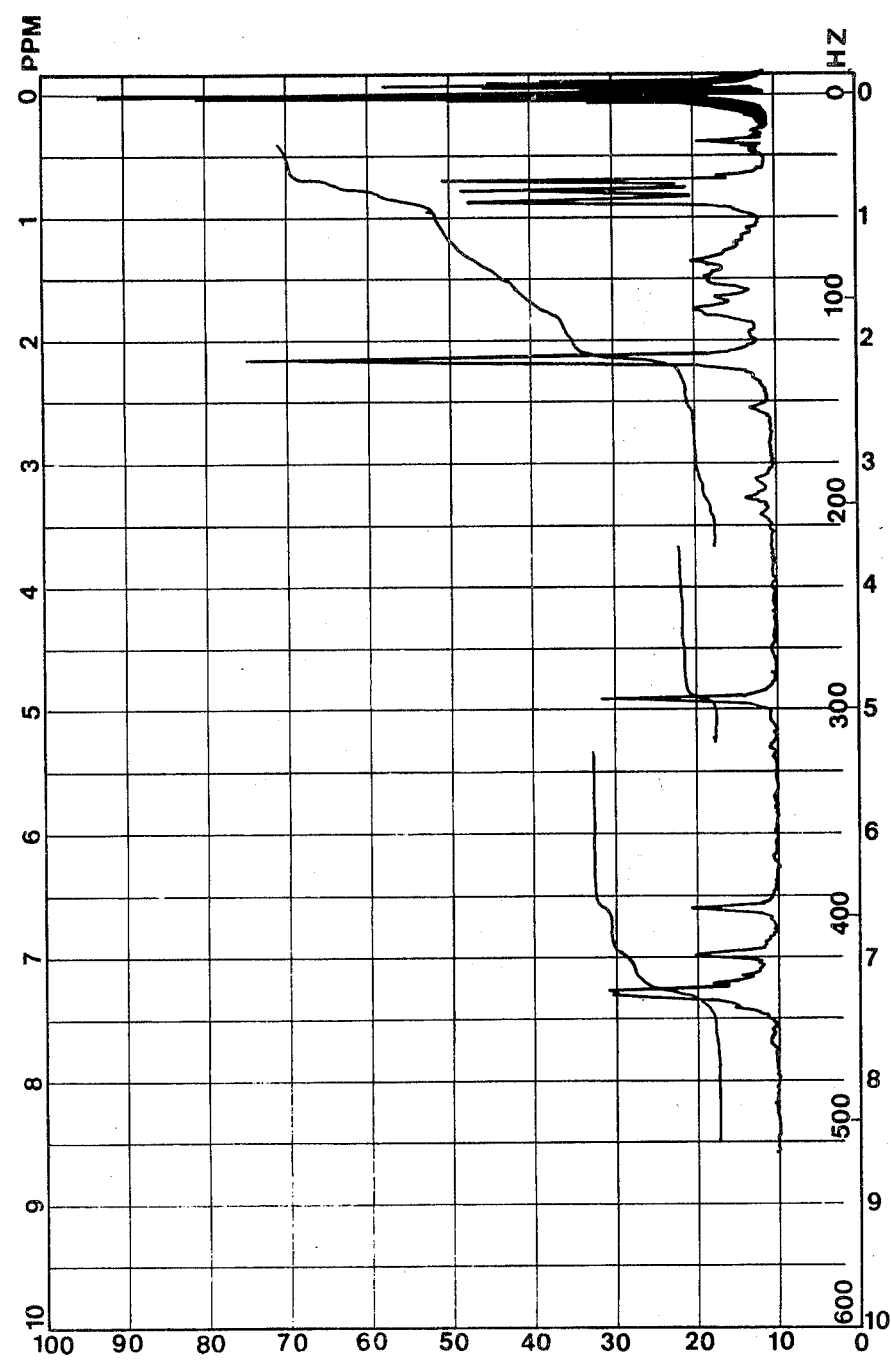

NMR See FIG. 4—The following signals are observed (d values), solvent CDCl$_3$:

0.70, 0.78, 0.87 (3 singlets, 3H each, camphane methyls) 1—2 (7H, complex system, camphane hydrogens) 2.15 (6H, wide singlet, aromatic methyls) 3.3 (1H, wide triplet, camphane-CH-bonded to the aromatic ring) 4.92 (2H, wide singlet, benzylic CH$_2$) 6.6 and 6.97 (2H, wide singlets, aromatic hydrogens) 7.3 (5H, complex system, C$_6$H$_5$)

Preparation of xybornol 0.5 g of 10% Pd on carbon and 1 ml of 70% HClO$_4$ are added to 10 g of xybornol benzylether dissolved in 100 ml of ethyl acetate and 30 ml of acetic acid. The mixture is then hydrogenated at atmospheric pressure, and 0.65 liters of hydrogen, referred to normal conditions, are consumed in a time of 15 minutes.

The catalyst is filtered through a layer of celite, the mixture is diluted with 100 ml of ethyl acetate and washed with 20 ml of water.

The organic layer is again washed with a 5% NaHCO$_3$ solution.

The solvent is evaporated to dryness to give a residue of 7.3 g of xybornol with a purity of 99% and a practically 100% yield.

After crystallising from methanol, the product has the following characteristics:

M.P.=94°-96° C.

Rf=0.33 (TLC with benzene-hexane 1:1 eluent—unitary product)

Figure 5:
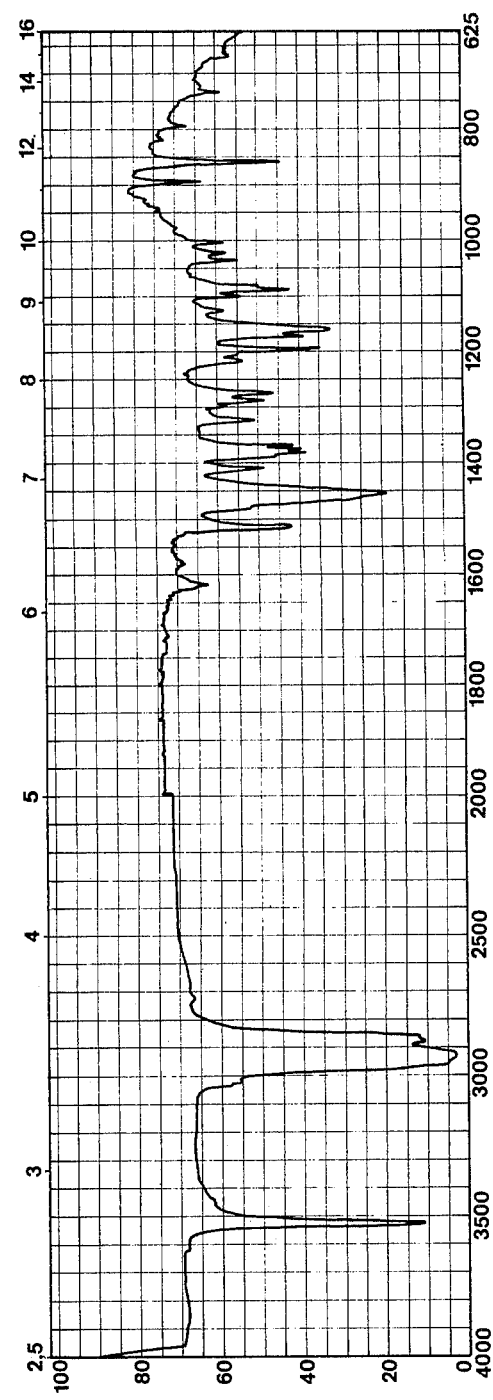

I.R.: see FIG. 5

Figure 6:
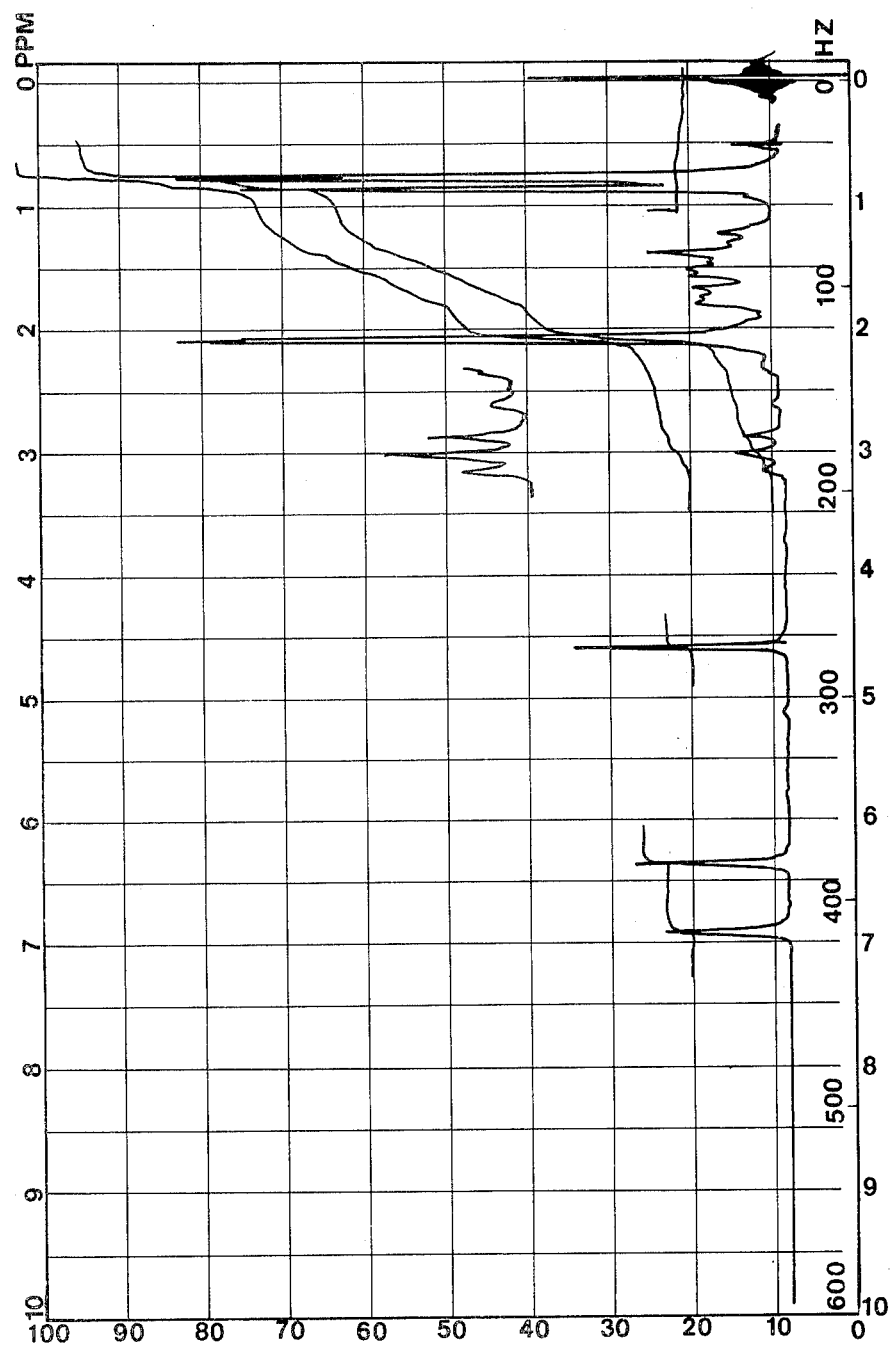

NMR: see FIG. 6. The following signals are observed (d values), solvent CDCl$_3$: 6.95 and 6.40 (2 singlets, 1H each, aromatic hydrogens) 4.62 (singlet, 1H, phenolic hydroxyl proton) 3.06 (wide triplet, 1H, camphane—CH—bonded to the aromatic ring) 2.15 (wide singlet, 6H, two aromatic methyls) 1.1 to 1.9 (complex system, 7H, camphane hydrogens) 0.78, 0.80 and 0.90 (3 singlets, 3H each, camphane methyls)/

The preparation of the xybornol was repeated several times as heretofore described, varying some operating conditions.

For example, in preparing the xybornol benzylether, CCl$_4$ and CH$_2$Cl$_2$ were used as the condensation solvent instead of the carbon disulphide, and AlCl$_3$ and BF were used as the condensation catalyst instead of SnCl$_4$.

In a further modification, during the hydrogenation stage, PtO$_2$ was used instead of the Pd catalyst, with ethyl acetate and acetic acid as solvent. In all cases, equivalent results were obtained, with limited fluctuations in the product yield and purity.

I claim:

1. A process for preparing 6-isobornyl-3,4-xylenol of formula

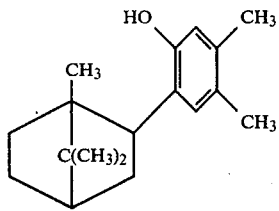

wherein camphene and 3,4-dimethylphenol benzylether are condensed in an inert anhydrous organic solvent in the presence of a Friedel-Crafts catalyst at a temperature of about 0° C., and the 6-isobornyl-3,4-xylenol benzylether thus obtained is debenzylated by hydrogenation in the presence of a hydrogenation catalyst chosen from the group consisting of Pb, Pt and their compounds.

2. A process as claimed in claim 1, wherein the Friedel-Crafts catalyst is chosen from the group consisting of $SnCl_4$, $BF_3$, $AlCl_3$, $SbCl_5$.

3. A process as claimed in claim 1, wherein the inert anhydrous organic solvent is chosen from the group consisting of $CS_2$, $CCl_4$, $CH_2Cl_2$, ethyl ether, benzene, nitrobenzene.

4. A process as claimed in claim 1, wherein hydrogenation is carried out in a solvent consisting of a mixture of ethyl acetate and acetic acid.

* * * * *